US010598761B2

(12) United States Patent
Coffeng

(10) Patent No.: US 10,598,761 B2
(45) Date of Patent: Mar. 24, 2020

(54) METHOD AND APPARATUS FOR TRACKING A DEVICE

(71) Applicant: GENERAL ELECTRIC COMPANY, Schenectady, NY (US)

(72) Inventor: Rene J. Coffeng, Helsinki (FI)

(73) Assignee: General Electric Company, Schenectady, NY (US)

( * ) Notice: Subject to any disclaimer, the term of this patent is extended or adjusted under 35 U.S.C. 154(b) by 241 days.

(21) Appl. No.: 15/602,548

(22) Filed: May 23, 2017

(65) Prior Publication Data

US 2017/0336491 A1 Nov. 23, 2017

(30) Foreign Application Priority Data

May 23, 2016 (GB) .................................. 1608999.7

(51) Int. Cl.
*G01S 3/02* (2006.01)
*G01S 5/02* (2010.01)
(Continued)

(52) U.S. Cl.
CPC ........... *G01S 5/0289* (2013.01); *G16H 10/60* (2018.01); *H04W 4/80* (2018.02); *G01S 5/02* (2013.01);
(Continued)

(58) Field of Classification Search
CPC ........ G01S 5/0289; G01S 5/02; G01S 5/0294; G01S 5/14; H04W 4/80; H04Q 9/00;
(Continued)

(56) References Cited

U.S. PATENT DOCUMENTS 6,270,457 B1 * 8/2001 Bardy .................. A61B 5/0002
600/300
7,978,062 B2 * 7/2011 LaLonde ............ A61N 1/37282
340/539.11
(Continued)

FOREIGN PATENT DOCUMENTS

| WO | 2004070546 A2 | 8/2004 |
| WO | 2005096568 A1 | 10/2005 |
| WO | 2008011063 A2 | 1/2008 |
| WO | 2008083285 A1 | 7/2008 |

OTHER PUBLICATIONS

Combined Search and Exam Report for corresponding GB Appln. No. 1608999.7, dated Nov. 9, 2016, 7 pages.
(Continued)

*Primary Examiner* — Chuong P Nguyen
(74) *Attorney, Agent, or Firm* — Andrus Intellectual Property Law, LLP

(57) ABSTRACT

A method for tracking a device not actively sending patient data to a network of medical devices is disclosed. The method comprises the device giving a signal at a time interval; an active hub listening to the device at the time interval; the active hub storing information about the device; and the active hub continuing to listen at the time interval to the device until the device actively sends patient data, or until no more signals are heard from the device. A system for tracking a device of a network of medical devices is also disclosed. The network comprises a hub and at least one device. The at least one device is configured to give a signal to the hub at a time interval, if the at least one device does not actively send patient data. The hub is configured to listen at the time interval to any devices not actively sending patient data. The hub is configured to store information about any devices not actively sending patient data. The hub is configured to continue listening to any devices not actively sending patient data until all devices actively send
(Continued)

patient data, or until no more signals are heard from any devices not actively sending patient data.

16 Claims, 2 Drawing Sheets

(51) Int. Cl.
*G16H 10/60* (2018.01)
*H04W 4/80* (2018.01)
*G01S 5/14* (2006.01)
*G01S 11/06* (2006.01)
*G06Q 10/08* (2012.01)
*H04Q 9/00* (2006.01)
*H04W 84/18* (2009.01)

(52) U.S. Cl.
CPC ............... *G01S 5/0294* (2013.01); *G01S 5/14* (2013.01); *G01S 11/06* (2013.01); *G06Q 10/087* (2013.01); *H04Q 9/00* (2013.01); *H04Q 2209/43* (2013.01); *H04W 84/18* (2013.01)

(58) Field of Classification Search
CPC ............ G08B 21/0202; G08B 21/0269; G08B 21/0272; G08B 21/0205; G08B 21/0288
USPC ................ 342/363, 463; 340/539.15, 539.13
See application file for complete search history.

(56) References Cited

U.S. PATENT DOCUMENTS

| | | | | |
|---|---|---|---|---|
| 8,823,527 | B2* | 9/2014 | Husen | G08B 21/06 340/573.1 |
| 9,007,202 | B1* | 4/2015 | Chan | G08B 21/0202 340/539.13 |
| 9,094,781 | B2* | 7/2015 | Wang | H04W 4/80 |
| 9,101,335 | B2* | 8/2015 | Coffeng | A61B 5/746 |
| 10,297,132 | B2* | 5/2019 | Fahey | A61B 5/0002 |
| 2015/0070187 | A1* | 3/2015 | Wiesner | A61B 5/0022 340/870.02 |
| 2015/0123786 | A1 | 5/2015 | Hasan et al. | |
| 2015/0154370 | A1* | 6/2015 | Skaaksrud | H04W 12/06 705/2 |
| 2016/0071392 | A1 | 3/2016 | Hankey et al. | |
| 2016/0117813 | A1* | 4/2016 | Gross | H04W 76/10 600/474 |
| 2019/0287661 | A1* | 9/2019 | Nobre | G16H 15/00 |

OTHER PUBLICATIONS

Dallas, Having a Heart Attack or Stroke? Your iPhone Knows, http://www.everydayhealth.com/heart-health/having-a-heart-attack-or-stroke-your-phone-knows-6152.aspx, dated Aug. 30, 2013, 4 pages.

Examination Report for corresponding GB Appln. No. 1608999.7, dated May 17, 2017, 4 pages.

* cited by examiner

METHOD AND APPARATUS FOR TRACKING A DEVICE

BACKGROUND

The present disclosure relates to tracking a device. More particularly, the present disclosure relates to tracking medical devices in networks of medical devices. More particularly, the present disclosure relates to a method for tracking a device not actively sending patient data to a network of medical devices and a system for tracking a device of a network of medical devices.

Devices are easily lost in large hospitals, because they are used occasionally at different places for different periods of time. An inventory list may show that there are a certain number of devices, but the inventory list does not state where they are or where they are after they have been used and moved. Often resources have to be used to search for them and sometimes they are found, but sometimes they are lost or not recovered when they are needed. Resources within a hospital are limited, especially staff resources, equipment and technical resources. Tracking or locating medical devices without having to install additional equipment for tracking or locating the device is not known.

SUMMARY OF THE INVENTION

The present disclosure is directed to a method for tracking a device not actively sending patient data to a network of medical devices and a system for tracking a device of a network of medical devices. This can be achieved by the features as defined by the independent claims. Further enhancements are characterized in the dependent claims.

According to one embodiment, the present disclosure is directed to a method for tracking a device not actively sending patient data to a network of medical devices. The method comprises: the device giving a signal at a time interval; an active hub listening to the device at the time interval; the active hub storing information about the device; and the active hub continuing to listen at the time interval to the device until the device actively sends patient data, or until no more signals are heard from the device. The time interval may be a time interval in the range of 5 seconds to 5 minutes, preferably 1 minute. The time period may comprise listening around one second and not listening for the remainder of the time period.

According to one embodiment, the device is a medical sensor with a battery, the medical sensor being connectable to the network. According to one embodiment, the information about the device comprises at least an identification number of the device and a location of the active hub. Preferably, the information is stored on a central database external to the hub.

According to one embodiment, the method may further comprise: if the device leaves the reach of the active hub and enters the reach of another active hub, then the another active hub takes over listening to the device from the active hub.

According to one embodiment, more than one active hub listens to the device and store information about the device. Preferably, the distance between the device and the more than one active hub is used for tracking and locating the device, and triangulation is used for locating the device and other devices.

According to one embodiment, the method further comprises that the device not actively sending patient data indicates that it is being tracked.

According to one embodiment, the present disclosure is directed to a system for tracking a device of a network of medical devices. The system comprises a hub and at least one device. The at least one device is configured to give a signal to the hub at a time interval, if the at least one device does not actively send patient data. The hub is configured to listen at the time interval to any devices not actively sending patient data. The hub is configured to store information about any devices not actively sending patient data. The hub is configured to continue listening to any devices not actively sending patient data until all devices actively send patient data, or until no more signals are heard from any devices not actively sending patient data. According to one embodiment, the time interval is a time interval in the range of 5 seconds to 5 minutes, preferably 1 minute. The time period may comprise listening around one second and not listening for the remainder of the time period.

According to one embodiment, the at least one device is medical sensor with a battery, the medical sensor being connectable to the network of medical devices. According to one embodiment, the information about any devices not actively sending patient data comprises at least an identification number of the device and a location of the active hub. Preferably, the system is configured to store the information on a central database external to the hub.

According to one embodiment, the system further comprises, if a device not actively sending patient data leaves the reach of the hub and enters the reach of another hub of a corresponding network of medical devices that can track devices, then the another hub is configured to take over listening to the device not actively sending patient data from the hub.

According to one embodiment, the more than one hub is configured to listen to any device not actively sending patient data and store information about any such devices. Preferably, the system is configured to use distance between any device not actively sending patient data and the more than one hub for tracking and locating any devices not actively sending patient data, and triangulation for locating any device not actively sending patient data.

According to one embodiment, the system is configured to indicate that the device not actively sending patient data is being tracked.

At least one embodiment disclosed herein provides a method and a system for tracking and locating a device of a network of medical devices. At least one embodiment disclosed herein provides a solution to only make limited use of technical resources, especially the available band width in networks. At least one embodiment avoids having to install additional equipment to track devices and provides a tracking system and method using existing equipment. At least one embodiment disclosed herein provides a solution that is inexpensive and easy to realize in reality. At least one of the embodiments disclosed herein provides one or more solutions to the problems and disadvantages with the background art. At least one embodiment avoids misplacing or loosing sensors in a hospital. At least one embodiment provides improved patient safety and/or improved quality of patient monitoring.

Other technical advantages of the present disclosure will be readily apparent to one skilled in the art from the following description and claims. Various embodiments of the present application obtain only a subset of the advantages set forth. No one advantage is critical to the embodiments. Any disclosed embodiment may be technically combined with any other disclosed embodiment or embodiments.

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

Figure 1:
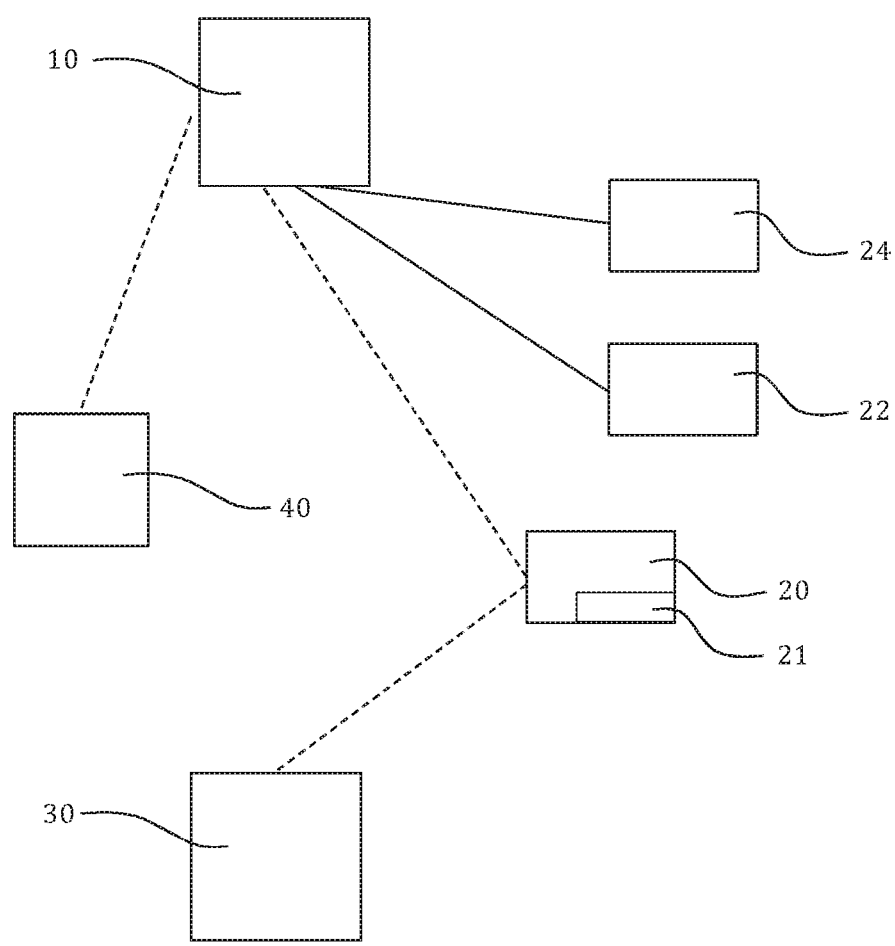
FIG. 1 is a diagrammatic illustration of a system according to an exemplary embodiment of the disclosure.

Sensors, for example medical sensors, medical devices, may get lost. When they are used and actively send patient data to a hub within a medical network, such as for example a medical body area network ("MBAN"), then they are normally not lost. However, when a sensor, a device, doesn't actively send patient data, then it may get lost. This happens for example with sensors not used, or a sensor that is used but taken of the subject, for example when the subject eats, moves around, or goes to the bathroom. At least one embodiment tracks and locates sensors by using network specific features and multiplexing of slots of existing equipment. By keeping an inactive sensor, a sensor not actively sending data, in an active network, for example a body area network, the last position of the sensor will be registered. Addressing technical resources, the bandwidth usage will be limited to a multiplexed slot at fixed time intervals, and use is made of the existing equipment not adding additional equipment. Looking at it in a parent child analogy, medical networks with hubs (parents) within the networks, act as a network of guarding parents, taking care of all children. Devices (children) such as for example sensors, will be kept a live link to, whenever they are not playing (actively sending patient data) with their own, or others, parent. A device not actively sending patient data may be regarded as a lost child calling for its parent (hub).

In at least one embodiment, one or more networks, such as a network in a hospital listens for example once every minute on a discovery slot for devices not actively sending patient data. In the parent child analogy it would be a parent listening every minute for any crying children. The crying child is for example a sensor scanning for beacons at multiple Wi-Fi frequencies every minute. An unassigned sensor tries to loosely connect (without NFC and key sharing) after beacon at synced clock of 01:00:000 seconds. Interval may be set based on expected clock drift, resynchronisation may be used if too much drift. Normally the network, the hub in the network, which the devices connect to is the last network they were being used with for measuring patient data. After the hub heard the cry, the hub confirm loosely paired and tell to repeat the keeping alive signal in the same or a different slot at 01:00:000+Y ms by means of a short cry. Next lost sensor at 01:00:000+N× 225+Y ms. Max amount of assigned sensors to one hub in a network may be for example 500. Thus, the parent hears the call of the child and tells the child to call for example every minute so that the parent continues to know where the child is. Any further lost children may also call but not exactly at the same time.

In at least one embodiment, lost devices may be easily traced and located. When a device is physically lost, for example the battery of the device is empty or almost empty, a user may activate a button on for example a server screen, for example a monitor. A network and its identification, for example a hub in the network, that has the device loosely coupled may sound and/or blink. Any devices that are loosely connected may blink for example once per 10 seconds for 10 minutes. If a lost device is out of power, then at least the last network that had the device, battery, in close proximity will be registered. The dB of the last cry may be used as an indication of distance in meters of the device from the hub and a manual search may be made.

In at least one embodiment, tracking or locating devices may not require additional equipment, such as for example RFID ports or additional parallel networks. The existing medical networks, and their hubs, may be sufficient. Devices not active may be kept paired, loosely paired, with the hub closest by, to keep track of their latest position without using significant bandwidth or battery power. Optionally, a device can loosely pair with two or more hubs allowing for triangulation based on dB signal strength for even more accurate positioning. A Wi-Fi discovery service may ask all hubs for example once per minute about all loosely paired batteries and their signal strengths. This may in turn be kept in a register or database for tracking and locating lost devices. Such an inventory list may be local to the medical network, or central to the hospital and its networks. In this way devices of a medical network, for example a MBAN, may be tracked and located by simply using network specific features and multiplexing of slots.

Turning to FIG. 1, according to at least one embodiment described herein, a hub 10 of a medical body area network ("MBAN") comprises devices 20, 22, and 24. Devices 22 and 24 may be active devices, for example, sending patient data actively to the hub 10, for example at a frequency of several times a second. Device 20 may be an inactive sensor. Device 20 has become inactive because the device 20 does not actively send data to the hub 10. Device 20 can become inactive for example because it is not used, or its battery is low, or the device is physically removed from one network to another network, or from one hub of a network to another hub of another network. Hub 10 is only listening to the device 20 at a certain interval, period of time. Another hub 30 may also, or instead, be listening to the device 20. The data concerning device 20 collected by the hubs 20 and 30 may be sent to a database 40. The different exemplary embodiments illustrated by FIG. 1 will be addressed in more detail below.

Figure 2:
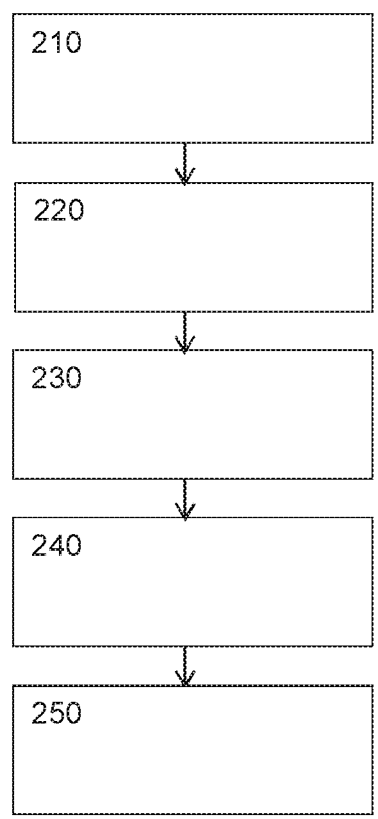
FIG. 2 shows a flow chart of a method according to an exemplary embodiment of the disclosure.

Turning to FIG. 2, a method for tracking a device not actively sending patient data to one or more networks of medical devices is disclosed. The method may comprise the following steps 210-250 taken in any order. Step 210, the device gives a signal at a time interval. Step 220, an active hub listens to the device at the time interval. Step 230, the active hub stores information about the device. Step 240, the active hub continues to listen at the time interval to the device until the device actively sends patient data, or until no more signals are heard from the device. In this way a device not actively sending patient data to one or more networks of medical devices can be tracked, and even located. The inactive device 20, for example a sensor, gives a signal to an active hub 10 at a time interval and the hub 10 therefore knows that the device is within its range. By utilizing the one or more features of the medical networks, for example MBAN, an inactive device can be tracked. By utilizing multiplexing of slots, for example only listening at a certain time interval, technical recourses, such as Wi-Fi band width, are able to be additionally used for tracking inactive devices. The active hub may be listening to more than only one device as described above.

According to at least one embodiment, the time interval is a time interval in the range of 5 seconds to 5 minutes, preferably 1 minute. The time interval is a time period where the signal is given by the device (the cry from the child) and the hub is listening (the parent is listening to the child) for a short part of the time period, and for the remaining part of the time period the signal is not given and the hub is not listening. This saves resources and battery. For example, for a time interval of one minute, the signal is given and the hub is listening, for example, for 1 second, and the signal is not given and the hub is not listening, for example, for 59 seconds. A suitable time interval may be any number of seconds from 5 seconds to 300 seconds (5 minutes) and of which more or less one second, or for example half a second, or for example two seconds, is the time when the signal is given and the hub is listening. This allows the battery of the inactive devices to last a very long time and the devices can be tracked as long as the battery last, which then may be several days. When the battery 21 is empty, then the hub "hearing" the device last can tell where the device was last heard.

In at least one embodiment, the device 20 is a medical sensor with a battery 21. The medical sensor may be connectable to the medical network, for example a MBAN. Preferably the device is a wireless device.

In at least one embodiment, the information about the device comprises at least an identification number of the device and a location of the active hub. The information may be stored on a central database external to the hub. The information may be stored only in one or more hubs. Such information may be part of an inventory list. Additionally, the time of the stored information may be recorded. Additionally, the position and/or identification number of the hub may be stored. In this way it is known where a device was last "heard". One or more hubs may be connected to a hospital network and the central database may be accessible through such a network. The hubs may update any other database, such as an inventory list, that is available for the hospital in question. However, the present disclosure is not limited to only hospitals, embodiments disclosed herein may also be used for other environments where devices may get lost, such as for example home care, sport facilities, etc.

In at least one embodiment, the method may further include a step 250 that is if the device 20 leaves the reach of the active hub 10 and enters the reach of another active hub 30, then the another active hub 30 takes over listening to the device 20 from the active hub 10. The other hub 30 takes over the listening at the time interval to the device not actively sending patient data. When the hub 30 picks up the task to listen to the device 20, then the hub 30 also stores the information about the device 20. The previous hub 10 may store information that now hub 30 is listening instead. According to one embodiment, the other hub 30 may be listening in addition to the first hub 10, i.e. the device 20 needs not to leave the reach of the hub 10.

According to one embodiment, the active hub stores information about the device not sending actively patient data when the active hub receives the signal from the inactive device, and the active hub continuing to listen at the time interval to the inactive device until the inactive device gets active, or until no more signals are heard from the inactive device.

According to at least one embodiment, more than one active hub listens to the device not actively sending patient data and store information about the device. According to a further embodiment, the distance between the device and the active hub, or the more than one active hub, is used for tracking and locating the device. The distance may be given by the dB of the signal, or other indication of the distance. One way of locating a device in this way may be by using triangulation. The distance between any hub and any inactive device may be stored so that when a device is required, then a location of the inactive device can be given.

According to one embodiment, the device not actively sending patient data may be given an indication that it is being tracked. For example the inactive device itself may show such an indicator on a screen or by a specific light indication. For example the active hub may communicate with the inactive device to switch the device to indicate that it is tracked. A user may thus see the indication on the inactive device and note that such an inactive device is being tracked or is lost.

Turning to FIG. 1, according to an embodiment a system for tracking a device 20 of a medical body area network ("MBAN") is disclosed. The system may comprise one or more networks and the one or more networks may be one or more networks of medical devices. The network comprises a hub 10, 30 and at least one device 20, 22, 24. The device is for example a sensor for medical measurements on a subject. The at least one device 20 is configured to give a signal to the hub 10 at a time interval, if the at least one device 20 does not actively send patient data. The hub 10 is configured to listen at the time interval to any devices 20 not actively sending patient data. The hub 10 is configured to store information about any devices not actively sending patient data. The hub 10 is configured to continue listening to any devices 20 not actively sending patient data until all devices actively send patient data, or until no more signals are heard from any devices not actively sending patient data. In the case where all devices actively send patient data, the device that was not actively sending patient data has become active by sending actively patient data and needs no tracking anymore because it is being used. In the case where no more signals are heard from any devices not actively sending patient data, the likely cause is that the battery 21 of the device 20 is flat, or that the device 20 is simply no more. In this way a device not actively sending patient data within a medical network may be tracked using the existing network features and multiplexing of slots. This also allows for the last position of the device to be registered.

According to at least one embodiment, the time interval is a time interval in the range of 5 seconds to 5 minutes, preferably 1 minute. For example, the time interval may be the hub listening every full minute for 1 second for devices not actively sending patient data. The time interval is a time period where the signal is given by the device (the cry from the child) and the hub is listening (the parent is listening to the child) for a short part of the time period, and for the remaining part of the time period the signal is not given and the hub is not listening. For example, for a time interval of one minute, the signal is given and the hub is listening, for example, for 1 second, and the signal is not given and the hub is not listening, for example, for 59 seconds. A suitable time interval may be any number of seconds from 5 seconds to 300 seconds (5 minutes) and of which more or less one second, or about half a second, or about 2 seconds, is the time when the signal is given and the hub is listening. This allows the battery of the inactive devices to last a very long time and the devices can be tracked as long as the battery last, usually several days. When the battery 21 is empty, then the hub "hearing" the device last can tell where the device was last heard.

In at least one embodiment, the device 20 is a medical sensor with a battery 21. The medical sensor may be configured to be connectable to the medical network, for example a MBAN. Preferably the device is a wireless device.

In at least one embodiment, the information about any devices not actively sending patient data comprises at least an identification number of the device and a location of the active hub. The system may be configured such that the information may be stored on a central database external to the hub. The system may be configured such that the information may be stored only in one or more hubs. The system may be configured to hold an inventory list. Additionally, the time of the stored information may be recorded. Additionally, the position and/or identification number of the hub may be stored. In this way it is known where a device was last "heard". One or more hubs may be connected to a hospital network and the central database may be accessible through such a network. The hubs may update any other database, such as an inventory list, that is available for the hospital in question. However, the present disclosure is not limited to only hospitals, it can also be used for other environments where devices may get lost, such as for example home care, sport facilities, etc.

In at least one embodiment, the system may further comprise if a device 20 not actively sending patient data leaves the reach of the hub 10 and enters the reach of another hub 30 of a corresponding network of medical devices that can track devices 20, then the another hub 30 is configured to take over listening to the device 20 not actively sending patient data from the hub 10. The other hub 30 takes over the listening at the time interval to the device not actively sending patient data. When the hub 30 picks up the task to listen to the device 20, then the hub 30 may also store the information about the device 20. The previous hub 10 may store information that now hub 30 is listening instead, and may additionally stop listening to the device 20. According to one embodiment, the other hub 30 may be listening in addition to the first hub 10.

According to one embodiment, the active hub 10 is configured for storing information about the device 20 not sending actively patient data when the active hub receives the signal from the inactive device, and the active hub continuing to listen at the time interval to the inactive device until the inactive device gets active, or until no more signals are heard from the inactive device.

According to one embodiment, more than one hub 10 is configured to listen to any device 20 not actively sending patient data and store information about any such devices. According to a further embodiment, the system is configured to use distance between any device 20 not actively sending patient data and the more than one hub 10, 30 for tracking and locating any devices 20 not actively sending patient data, and triangulation for locating any device not actively sending patient data. Signal strength, dB, may be used for accessing distance. One way of locating a device in this way may be by using triangulation. The distance between any hub 10, 30 and any inactive device 20 may be stored so that when a device is required, then a location of the inactive device can be given.

According to one embodiment, the system is configured to indicate that the device 20 not actively sending patient data is being tracked. For example the inactive device itself may show such an indicator on a screen or by a specific light indication. For example the active hub 10 may communicate with the inactive device 20 to switch the device to indicate that it is tracked. A user may thus see the indication on the inactive device 20, and/or hub 10, and note that such an inactive device 20 is being tracked, or lost.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for tracking a device for a medical body area network (MBAN), the device being a medical sensor not actively sending patient data to the MBAN, the method comprising:
   the device giving a signal at a time interval;
   an active hub listening to the device at the time interval;
   the active hub storing information about the device; and
   the active hub continuing to listen at the time interval to the device until the device actively sends patient data, or until no more signals are heard from the device; and
   storing when no more signals are heard from the device an identifier of the device and a location of the active hub.

2. The method according to claim 1, wherein the time interval is a time interval in the range of 5 seconds to 5 minutes, preferably 1 minute.

3. The method according to claim 1, wherein the device is a medical sensor with a battery, the medical sensor being connectable to the MBAN.

4. The method according to claim 1, further comprising:
   if the device leaves the reach of the active hub and enters the reach of another active hub, then the another active hub takes over listening to the device from the active hub.

5. The method according to claim 1, wherein more than one active hub listens to the device and stores information about the device.

6. The method according to claim 5, wherein distance between the device and the more than one active hub is used for tracking and locating the device, and triangulation is used for locating the device and other devices.

7. The method according to claim 1, wherein the information is stored on a central database external to the hub.

8. The method according to claim 1, further comprising that the device not actively sending patient data indicates that it is being tracked.

9. A system for tracking a device of a medical body area network (MBAN) of medical devices, the MBAN comprising a hub and at least one device,
   the at least one device being configured to give a signal to the hub at a time interval, if the at least one device does not actively send patient data;
   the hub being configured to listen at the time interval to any devices not actively sending patient data;
   the hub being configured to store information about any devices not actively sending patient data; and
   the hub being configured to continue listening to any devices not actively sending patient data until all devices actively send patient data, or until no more signals are heard from any devices not actively sending patient data, and to store when no more signals are heard from one device among the devices an identifier of the one device and a location of the hub.

10. The system according to claim 9, wherein the time interval is a time interval in the range of 5 seconds to 5 minutes, preferably 1 minute.

11. The system according to claim 9, wherein the at least one device is medical sensor with a battery, the medical sensor being connectable to the MBAN of medical devices.

12. The system according to claim 9, further comprising:
if a device not actively sending patient data leaves the reach of the hub and enters the reach of another hub of a corresponding MBAN of medical devices that can track devices, then the another hub is configured to take over listening to the device not actively sending patient data from the hub.

13. The system according to claim 9, wherein more than one hub is configured to listen to any device not actively sending patient data and store information about any such devices.

14. The system according to claim 13, wherein the system is configured to use distance between any device not actively sending patient data and the more than one hub for tracking and locating any devices not actively sending patient data, and triangulation for locating any device not actively sending patient data.

15. The system according to claim 9, wherein the system is configured to store the information on a central database external to the hub.

16. The system according to claim 9, wherein the system is configured to indicate that the device not actively sending patient data is being tracked.

* * * * *